(12) United States Patent
Sanchez Martinez

(10) Patent No.: US 8,360,958 B2
(45) Date of Patent: Jan. 29, 2013

(54) APPARATUS FOR LENGTHENING THE PENIS

(76) Inventor: Alvaro Sanchez Martinez, Madrid (ES)

( * ) Notice: Subject to any disclaimer, the term of this patent is extended or adjusted under 35 U.S.C. 154(b) by 533 days.

(21) Appl. No.: 12/663,051

(22) PCT Filed: May 29, 2008

(86) PCT No.: PCT/ES2008/000382
§ 371 (c)(1),
(2), (4) Date: Apr. 12, 2010

(87) PCT Pub. No.: WO2008/148902
PCT Pub. Date: Dec. 11, 2008

(65) Prior Publication Data
US 2010/0204543 A1    Aug. 12, 2010

(30) Foreign Application Priority Data
Jun. 4, 2007 (ES) .............................. 200701186 U

(51) Int. Cl.
*A61F 5/00* (2006.01)
(52) U.S. Cl. ........................................................ 600/39
(58) Field of Classification Search .............. 600/38–41; 128/897–898
See application file for complete search history.

(56) References Cited

U.S. PATENT DOCUMENTS

| 764,801 A * | 7/1904 | Emerson ........................... 600/39 |
| 853,410 A * | 5/1907 | Huebner ........................... 600/39 |
| 2004/0215055 A1 | 10/2004 | Gomez-de-Diego |
| 2005/0124854 A1 | 6/2005 | Suchy |

FOREIGN PATENT DOCUMENTS

| DE | 202006011087 | 9/2006 |
| ES | 1044139 | 3/2000 |
| ES | 1048776 | 9/2001 |
| WO | 9626691 | 9/1996 |

* cited by examiner

*Primary Examiner* — Samuel Gilbert
(74) *Attorney, Agent, or Firm* — Sturm & Fix LLP

(57) ABSTRACT

Apparatus for lengthening the penis, said apparatus designed to support itself on the user's pelvis and comprising a substantially ring-shaped base element, wherefrom extend a pair of telescopic arms which join at the opposite end thereof to a bridge element having means of fastening to the penis, said arms articulated to the base element in such a way as to enable an angular movement with respect to a plane parallel to the base element, wherein the base element is coupled to a substantially ring-shaped lower base by means of rotation so that the base element is rotatable with respect to the lower base and the central longitudinal axis coinciding with the longitudinal axis of the penis. Thus with two rotational axes available the user has the option of choosing the most comfortable penis position and can rotate the upper bridge in ascending-descending direction and right-left direction simultaneously.

7 Claims, 6 Drawing Sheets

FIG.3
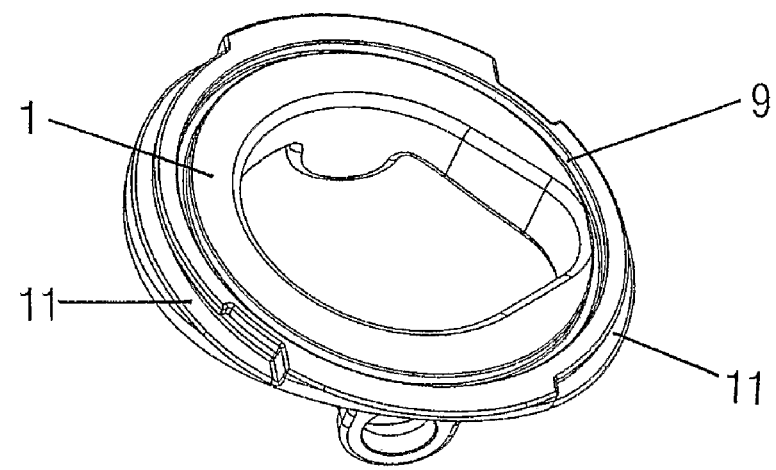
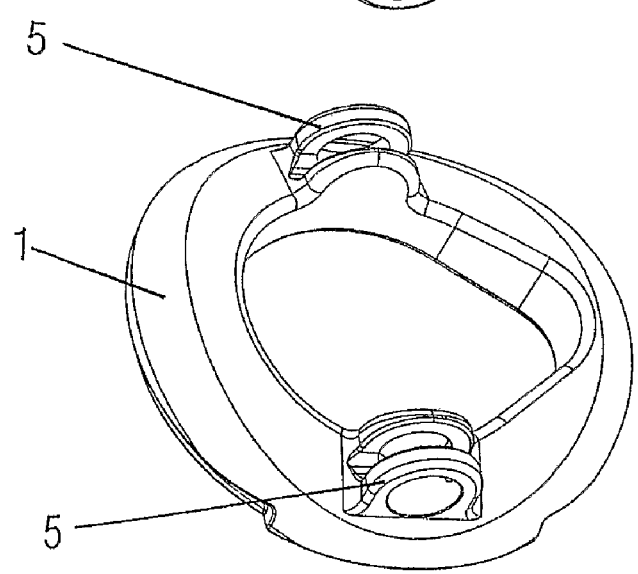
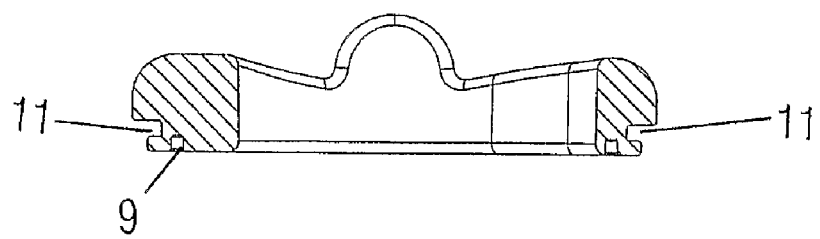

FIG.4
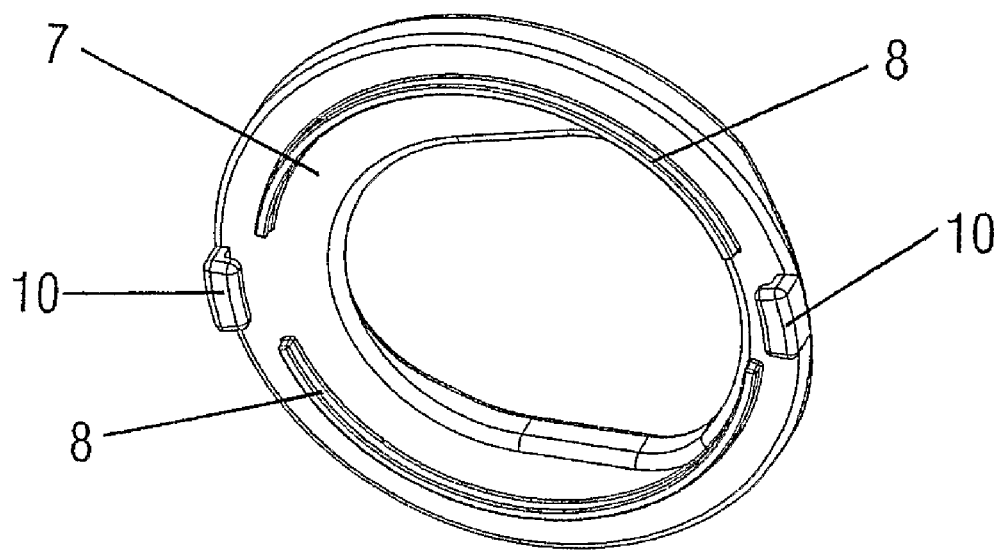
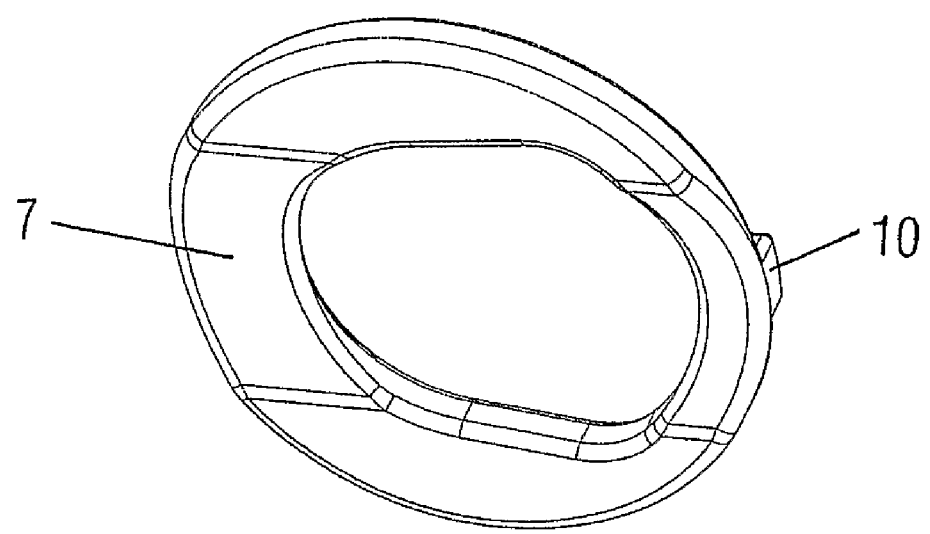

APPARATUS FOR LENGTHENING THE PENIS

OBJECT OF THE INVENTION

The object of the present application is to provide an apparatus for lengthening the penis that has significant innovations and advantages compared to other devices with the same purpose.

More specifically, the invention relates to an apparatus for lengthening the penis being of the type that comprises a substantially ring shaped base element designed to support itself on the area corresponding to the pelvis of the user, wherefrom extend a pair of telescopic arms which are joined at the opposite end thereof to a bridge element having fastening means to the penis, said arms being articulated to the base element so that it allows an angular movement in regard to a plane parallel to the base element.

BACKGROUND TO THE INVENTION

Apparatus have been known for some years that allow for the lengthening of the male sexual organ in a simple and effective manner that advantageously avoids any type of surgical operation with the discomfort that these can bring by means of the continued use of the same for a predetermined period of time.

For example, the Spanish Utility Model No ES 1 048 776 and the European Patent No EP 1 473 000 describe an apparatus to achieve the lengthening of the male organ in a progressive manner of the same type as the invention whose essential features are described and which form the preamble of Claim 1 of the invention.

However, all of the already known apparatus in the technique only allow the rotation along a single plane of the telescopic arms in regard to the base element therefore said apparatus can provide little comfort for the user whilst it is being used as it is well known that the penis is able to rotate or move along multiple planes and hence, the apparatus limits the position of the penis of the user in the apparatus.

DESCRIPTION OF THE INVENTION

The present invention has been developed for the purpose of providing an apparatus for the lengthening of the penis that solves the above-mentioned disadvantages, in addition contributing other additional advantages that will become clear from the description that is given below.

It is therefore an object of the invention to provide an apparatus for the lengthening of the penis being of the type that comprises a substantially ring shaped base element designed to support itself on the user's pelvis, wherefrom extend a pair of telescopic arms which are joined at the opposite end thereof to a bridge element having fastening means to the penis, said arms being articulated to the base element so that it allows an angular movement in regard to a plane parallel to the base element, and it is characterised in that the base element is coupled to an additional substantially ring shaped lower base by rotation means in such a way that the base element is additionally rotable in regard to the lower base and the longitudinal central axis coinciding with the longitudinal axis of the penis.

Thanks to these features, a new apparatus is obtained allowing to carry out a lengthening of the penis in a progressive and adjustable manner that unlike the other already known apparatus, allows the user to choose the position of the penis that is the most comfortable because of having two rotation axes or degrees of freedom, this means, being able to rotate the upper bridge in an ascending-descending and right-left direction in a simultaneous manner. Another use that the apparatus herein described may have is that it can be used on those people who suffer from Peyronie disease or curvature of the penis; hence it can be used as correction element.

In a preferred embodiment, the stated rotation means consists of curved path ribs that extend outwards from upper face of the lower base designed to fit into coinciding grooved portions in their position in regard to the ribs acting as a guiding means, and mobile gripping means that hold in a bonded state the base element and the lower base.

Preferently the mobile gripping means consists of some tabs that extend from the lower base that are fixed into some corresponding grooves by way of being guides provided on the side wall of the base element.

According to another aspect of the invention, the apparatus is provided with time control means so allowing the user to control the treatment time for the purpose of improving the effectiveness of the treatment, said time control means being a chronometer that is housed in one of the lateral ends of the bridge element.

According to another feature of the invention apparatus, each one of the articulated arms is mainly formed by two tubular elements having differing diameters fitted together capable of moving longitudinally in regard to the other, internally having been provided with anti-rotation means so as to prevent the rotation of one of the tubular elements with regard to the other tubular element.

Preferably, said anti-rotation means consists of a retaining element arranged in one end of the tubular element that is partially fitted into the other tubular element, said retaining element being formed by elastic protrusions that project outwards around the perimeter and in contact with the inner wall of the greater diameter tubular element, in such a way that in a rotation state of the tubular element movement with the smaller diameter, the tubular element with the greater diameter does not rotate unlike the known apparatus in which both elements rotate.

Other features and advantages of the penis lengthening apparatus object of the present invention will become clear from the description of a preferred embodiment, but it is not exclusive, the drawings that are attached are by way of illustration but without being in any way limiting.

BRIEF DESCRIPTION OF THE DRAWINGS

FIG. 3. This is an expanded upper and lower perspective view and a transversal section of the base element;

FIG. 4. This is an upper and lower enlarged perspective view of the lower base element.

DESCRIPTION OF A PREFERRED EMBODIMENT

In the light of the attached figures, an embodiment of the penis lengthening apparatus is shown, comprising a base element 1 made from plastic material and which is substantially ring shaped designed to support itself on the user's pelvis or lower abdomen, in which the penis of the user passes across a through central opening, wherefrom extend a pair of telescopic arms 2, 3 which are joined at the opposite end thereof to a bridge element 4 also made from plastic material, whose bridge element 4 is provided with known fastening means 13 to the penis and in turn acts as a support element at the end area of the penis. Such fastening means can consist of a rope or the like that is fastened to the bridge element 4 by some provided openings, such means being well known by those experts in the matter hence they are not going to be stated in greater detail.

Figure 5:
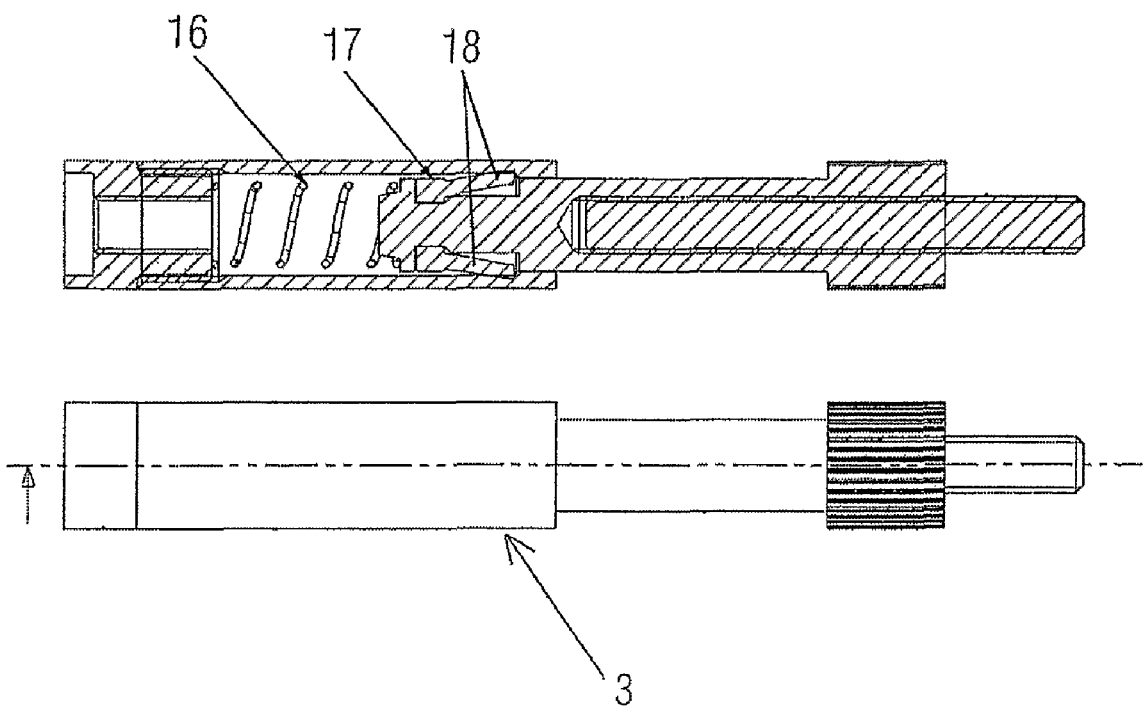
FIG. 5. This is a raised and longitudinal section corresponding to one of the telescopic arms.

Said arms 2, 3 being articulated to the base element 1 by means of an axis 12 fitted into some protrusions 5 that extend in an ascending direction from the upper part of the base element 1, in such a way that they allow angular movement of said arms 2, 3 in regard to a plane parallel to the base element 1. As shown, such protrusions consist of a pair of tabs facing each other. Each articulated arm 2, 3 is principally formed by two differing diameter tubular elements of differing diameters fitted to one another capable of being longitudinally moved in regard to the other and in addition having provided inside of one of the tubular elements, internal springs 16 that allow to maintain a stretching stress on the penis during treatment, as shown in FIG. 5. This stress can be regulated by rotating one of the tubular elements on the fixing stud 6 to the joint.

Figure 1:
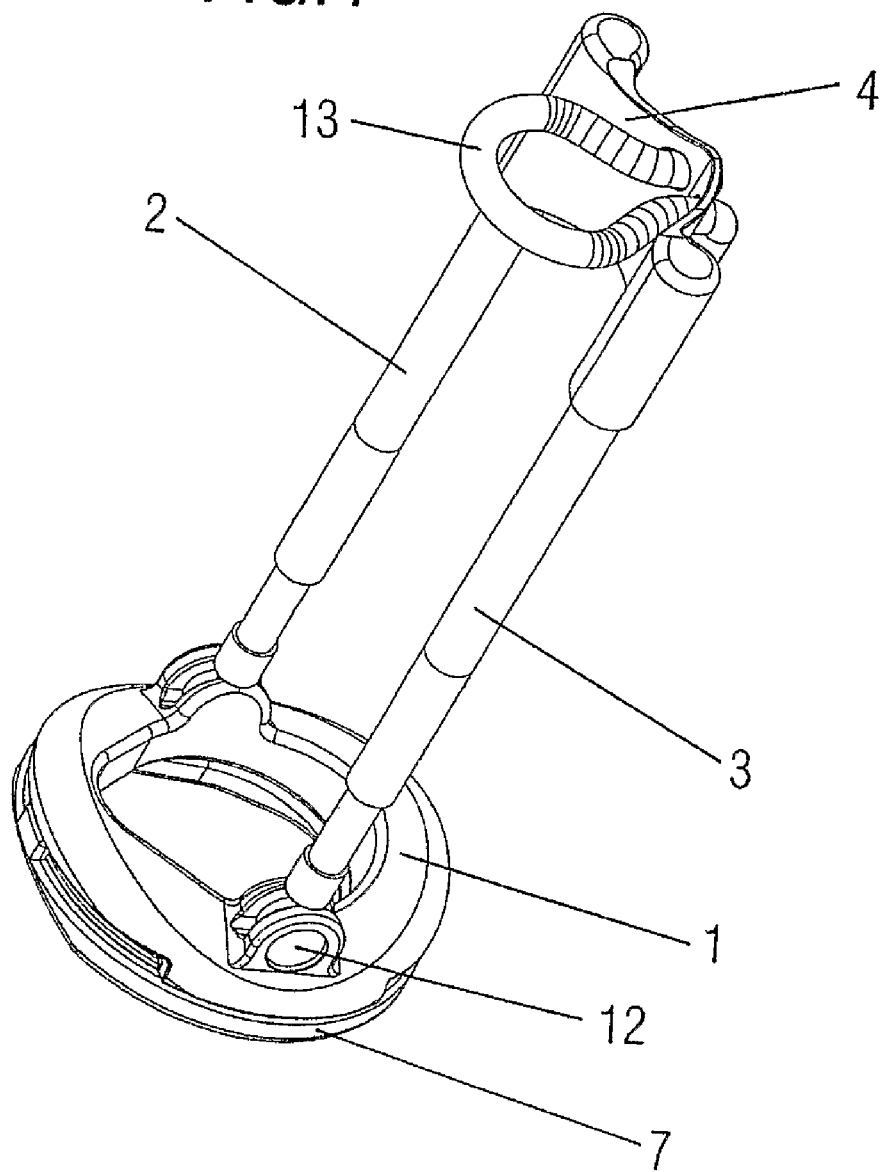
FIG. 1. This is a perspective view of a penis lengthening apparatus according to the present invention.
Figure 2:
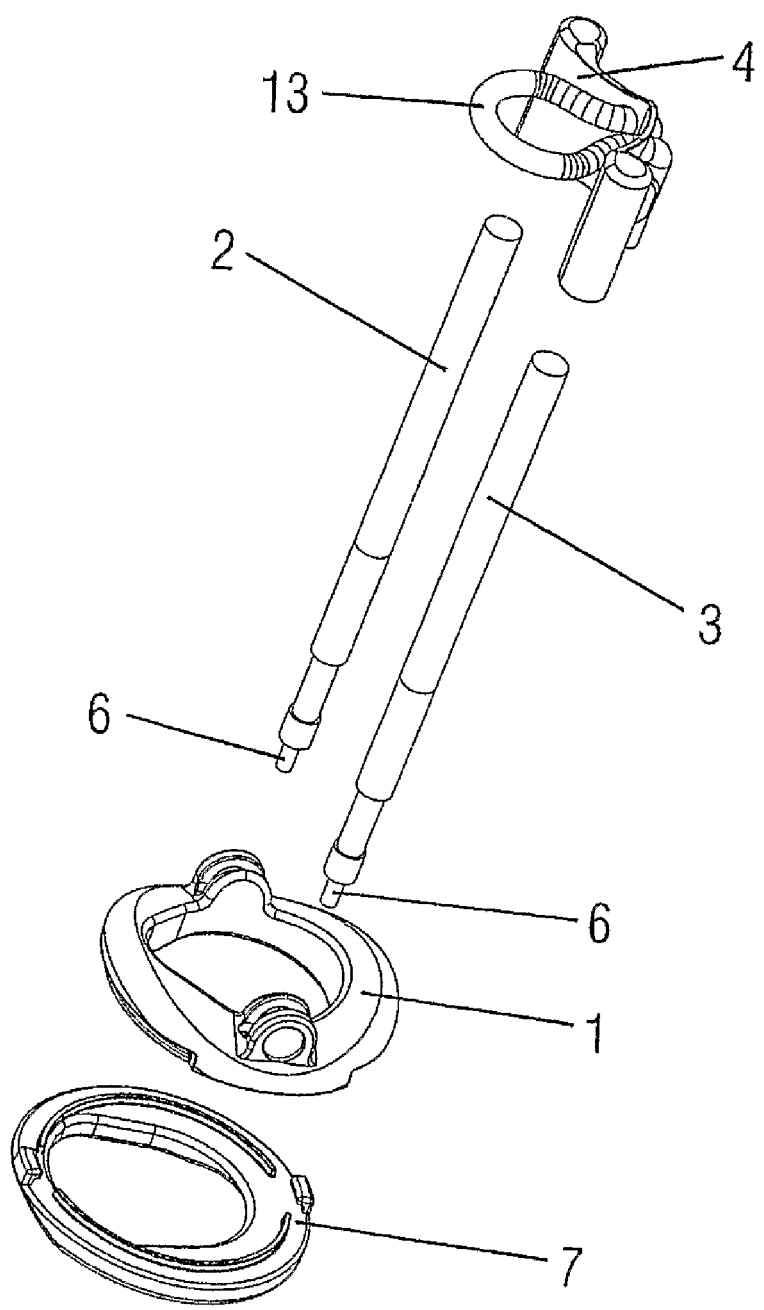
FIG. 2. This is a perspective exploded view of the assembly of the apparatus represented in the previous figure.

The base element 1 is fitted in a rotatory manner to a lower base 7 that also is in general substantially ring shaped by rotation means described later, in such a way that the base element 1 is rotable in regard to the lower base 7 and the central longitudinal axis coinciding with the longitudinal axis of the penis, whereby the bridge 4 can be moved in an ascending-descending and right-left direction, as and how shown by means of the arrows shown in FIG. 1.

Said rotation means consists of a pair of ribs 8 with a semi-circular shape and diametrically opposite which extend outwards from the upper face of the lower base 7 designed to be fitted into groove sections 9, their position coinciding with the ribs 8 acting by way of guide means, and mobile gripping means that hold the base element 1 and the lower base 7 in a bonded state, as can be seen in greater detail in FIGS. 3 and 4. In addition anti-rotation means is provided, the purpose of which is to prevent the rotation of one of the tubular elements in regard to the other tubular element, said anti-rotation means being formed by a retaining element 17 arranged in one end of the tubular element that is partially fitted into the other tubular element. As can be seen, the retaining element 17 comprises some elastic protrusions 18 that extends towards the perimeter and which are in contact with the inner wall of the greater diameter tubular element, so that in a rotation state of the movement of the smaller diameter tubular element, the greater diameter tubular element does not rotate.

In regard to the stated mobile gripping means these basically consist of a pair of tabs 10 that are diametrically opposite see FIG. 4 that extend from the lower base 7 which are fitted into some slots 11 provided externally on the side wall of base element 1.

Figure 6:
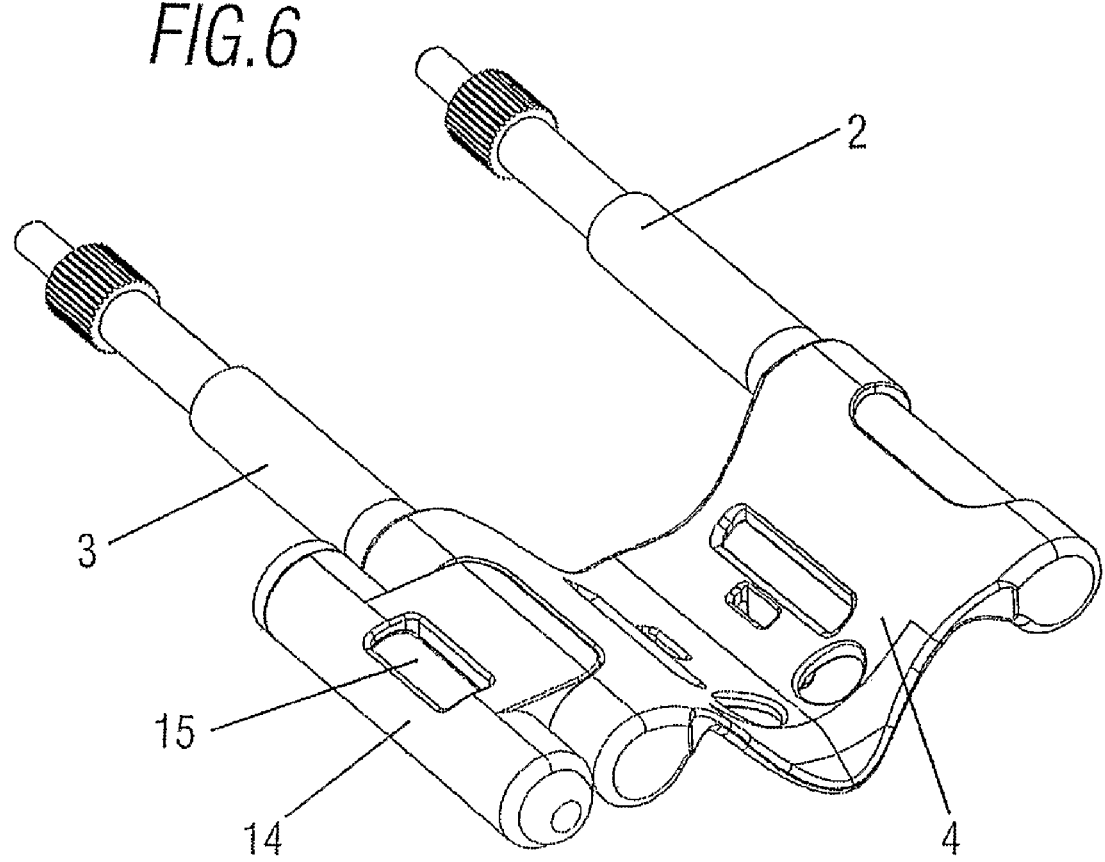
FIG. 6. This is a perspective view of an embodiment of the invention apparatus that comprises a chronometer to control the time and in which some pieces of same have been omitted.

In an additional manner, the apparatus of the invention is provided with time control means which consists of a reduced size chronometer 14 (see FIG. 6) with a display 15 that can easily be seen by the user and that is housed in one of the outer sides of the bridge element 4 by means of a fixing system assisting in the engagement and removal of the chronometer 14 in a simple and quick manner, in such a way that it allows the user to know the usage time so as to achieve greater effectiveness in the treatment.

The details, shapes, sizes and other accessoral elements, likewise the materials used in the manufacture of the apparatus for the lengthening of the penis of the invention can be appropriately substituted by others that are technically equivalent and do not stray away from the essentiality of the invention or the scope defined by the claims that are included below.

The invention claimed is:

1. Apparatus for the lengthening of the penis comprising a substantially ring shaped base element designed to support itself on the user's pelvis, wherefrom extend a pair of telescopic arms which are joined at the opposite end thereof to a bridge element having fastening means adapted to connect to the penis, said arms being articulated to the base element so that it allows an angular movement in regard to a plane parallel to the base element, characterised in that the base element is coupled to a substantially ring shaped lower base by means of rotation means in such a way that the base element is rotable in regard to the lower base and the longitudinal central axis coinciding with the longitudinal axis of the penis.

2. Apparatus for the lengthening of the penis according to claim 1, characterised in that the rotation means consists of curved path ribs that extends outwards from upper face of the lower base designed to fit in coinciding grooved portions in their position in regard to the corresponding ribs acting by way of guide means, and mobile gripping means that hold in a bonded state the base element and the lower base.

3. Apparatus for the lengthening of the penis according to claim 1, characterised in that the mobile gripping means consists of a pair of tabs, preferently diametrically opposite, which extend from the lower base designed to be fitted into some corresponding grooves by way of guides provided on the side wall of the base element by means of which said tabs can be moved.

4. Apparatus for the lengthening of the penis according to claim 1, characterised in that it is provided with time control means.

5. Apparatus for the lengthening of the penis according to claim 1, characterised in that said time control means consists of a chronometer of removable type which is housed in one of the side ends of the bridge element.

6. Apparatus for the lengthening of the penis according to claim 1, characterised in that each one of the articulated arms is mainly formed by two differing diameter tubular elements fitted together capable of moving longitudinally in regard to the other, internally having been provided with anti-rotation means so as to prevent the rotation of one of the tubular elements with regard to the other tubular element.

7. Apparatus for the lengthening of the penis according to claim 6, characterised in that said anti-rotation means consists of a retaining element arranged in one end of the tubular element that is partially fitted into the other tubular element, said retaining element being formed by elastic protrusions that extend outwards around the perimeter and that are in contact with the inner wall of the greater diameter tubular element, in such a way that in a rotation state of the movement of the smaller diameter tubular element, the greater diameter tubular element does not rotate.

* * * * *